United States Patent
Doki et al.

(10) Patent No.: US 10,739,280 B2
(45) Date of Patent: Aug. 11, 2020

(54) RADIATION PHASE CONTRAST IMAGING APPARATUS

(71) Applicant: Shimadzu Corporation, Kyoto (JP)

(72) Inventors: Takahiro Doki, Kyoto (JP); Kenji Kimura, Kyoto (JP); Taro Shirai, Kyoto (JP); Satoshi Sano, Kyoto (JP); Akira Horiba, Kyoto (JP); Naoki Morimoto, Kyoto (JP)

(73) Assignee: Shimadzu Corporation, Nakagyo-ku, Kyoto-shi, Kyoto (JP)

( * ) Notice: Subject to any disclaimer, the term of this patent is extended or adjusted under 35 U.S.C. 154(b) by 206 days.

(21) Appl. No.: 16/115,875

(22) Filed: Aug. 29, 2018

(65) Prior Publication Data
US 2019/0072501 A1   Mar. 7, 2019

(30) Foreign Application Priority Data

Sep. 6, 2017   (JP) .................. 2017-171006

(51) Int. Cl.
*G01N 23/041* (2018.01)
*A61B 6/00* (2006.01)
*A61B 6/04* (2006.01)

(52) U.S. Cl.
CPC ......... *G01N 23/041* (2018.02); *A61B 6/0407* (2013.01); *A61B 6/4291* (2013.01); *A61B 6/44* (2013.01); *A61B 6/484* (2013.01); *A61B 6/508* (2013.01); *A61B 6/589* (2013.01); *G01N 2223/3308* (2013.01); *G01N 2223/40* (2013.01)

(58) Field of Classification Search
CPC ....... A61B 6/484; A61B 6/4291; A61B 6/508; A61B 6/0407; G01N 23/041; G01N 2223/3306
See application file for complete search history.

(56) References Cited

U.S. PATENT DOCUMENTS

| | | | | |
|---|---|---|---|---|
| 7,889,838 | B2* | 2/2011 | David | A61B 6/4233 378/36 |
| 9,649,082 | B2* | 5/2017 | Wischmann | A61B 6/06 |
| 10,420,521 | B2* | 9/2019 | Roessl | G21K 1/06 |
| 2012/0243658 | A1* | 9/2012 | Geller | A61B 6/4291 378/16 |
| 2013/0142307 | A1* | 6/2013 | Nakamura | G01N 23/041 378/62 |

FOREIGN PATENT DOCUMENTS

WO   2009/104560 A1   8/2009

OTHER PUBLICATIONS

Pfeiffer, et al. "Phase retrieval and differential phase-contrast imaging with low-brilliance X-ray sources", Nat. Phys., vol. 2, pp. 258-261. Mar. 26, 2006.

* cited by examiner

*Primary Examiner* — David P Porta
*Assistant Examiner* — Fani Boosalis
(74) *Attorney, Agent, or Firm* — Muir Patent Law, PLLC

(57) ABSTRACT

The radiation phase contrast imaging apparatus includes an X-ray source, a first grating, a second grating arranged between the X-ray source and the first grating, and a moving mechanism for moving an object stage for holding an object. The moving mechanism is configured to more the object stage to an X-ray source side of the first grating and a second grating side of the first grating opposite to the source side of the first grating.

8 Claims, 15 Drawing Sheets

Relationship Between Position of Object and Scaling Ratio of Phase Contrast Image Relationship Between Position of Object and Scaling Ratio of Phase Contrast Image Relationship Between Position of Object and Contrast in Phase Contrast Image Relationship Between Position of Object and Contrast in Phase Contrast Image Relationship Between Position of Object and Contrast in Phase Contrast Image Relationship Between Position of Object and Contrast in Phase Contrast Image Relationship Between Scaling Ratio of Phase Contract Image and Contrast in Phase Contrast Image Relationship Between Scaling Ratio of Phase Contract Image and Contrast in Phase Contrast Image

RADIATION PHASE CONTRAST IMAGING APPARATUS

CROSS-REFERENCE TO RELATED APPLICATIONS

The priority application number JP 2017-171006, entitled "RADIATION PHASE CONTRAST IMAGING APPARATUS", filed on Sep. 6, 2017, invented by Takahiro Doki, Kenji Kimura, Taro Shirai, Satoshi Sano, Akira Horiba, and Naoki Morimoto, upon which this patent application is based is hereby incorporated by reference.

BACKGROUND OF THE INVENTION

Field of the Invention

The present invention relates to a radiation phase contrast imaging apparatus, and more particularly to a radiation phase contrast imaging apparatus for generating a phase contrast image based on a phase shift of X-rays.

Background Technique

Conventionally, a radiation phase contrast imaging apparatus for generating a phase contrast image based on a phase shift of X-rays is known. Such an X-ray phase contrast imaging apparatus is disclosed in, for example, International Patent Publication No. WO 2009/104560.

In International Patent Publication No. WO 2009/104560, an X-ray imaging apparatus (radiation phase contrast imaging apparatus) is disclosed in which an X-ray source for generating X-rays, a first grating for diffracting the X-ray generated from the X-ray source, a second grating for generating a moire pattern by further diffracting the X-ray diffracted by the first grating, and an X-ray image detector (image signal detector) for detecting the moire pattern generated by the second grating are provided. The X-ray imaging apparatus of International Patent Publication No. WO 2009/104560 is configured to perform X-ray imaging of an object by arranging the object between the X-ray source and the first grating to generate a phase contrast image based on the phase shift of the X-ray caused by the object.

In the X-ray imaging apparatus of International Patent Publication No. WO 2009/104560, the level of contrast in the phase contrast image has a negative correlation with the distance of the object from the first grating. Therefore, in the X-ray imaging apparatus of International Patent Publication No. WO 2009/104560, the position of the subject where the visibility (visible contrast) thereof can be secured in the phase contrast image is set within a range closer to the first grating between the X-ray source and the first grating.

Here, in the radiation phase contrast imaging apparatus of International Patent Publication No. WO 2009/104560, the scaling ratio (enlargement/reduction ratio) of the object in the phase contrast image depends on the distance of the object from the X-ray source. Therefore, in order to change the scaling ratio, it is necessary to change the position of the object between the X-ray source and the image signal detector along the optical axis direction of the X-ray. However, in the radiation phase contrast imaging apparatus of International Patent Publication No. WO 2009/104560, since the object is arranged between the X-ray source and the first grating, the range in which the position of the object can be changed in the optical axis direction is limited to the X-ray source side of the first grating. Therefore, it is considered that there is a problem that, assuming that the visibility in the phase contrast image is secured, the variable range of the scaling ratio of the object in the phase contrast image is likely to be limited to the range closer to the first grating on the X-ray source side of the first grating.

SUMMARY OF THE INVENTION

The present invention has been made to solve the aforementioned problems, and one of the objects of the present invention is to provide a radiation phase contrast imaging apparatus capable of expanding a variable range of a scaling ratio of an object while securing visibility in a phase contrast image.

In order to attain the aforementioned objects, a radiation phase contract imaging apparatus according to one aspect of the present invention includes an image signal generation system including an X-ray source and an image signal detector for detecting an image signal based on X-rays irradiated from the X-ray source; a plurality of gratings including a first grating arranged between the X-ray source and the image signal detector to receive the X-rays irradiated from the X-ray source and a second grating arranged between the first grating and the image signal detector; an image processing unit configured to generate a phase contrast image due to a phase shift of the X-ray caused by an object arranged between the X-ray source and the image signal detector; an object stage configured to hold the object; and a moving mechanism configured to move the object stage to an X-ray source side of the first grating and a second grating side of the first grating in an optical axis direction of the X-ray across the first grating. The first grating may be positioned to form a self-image with the X-rays irradiated from the X-ray source and the second grating may be positioned to cause interference with the self-image of the first grating.

In the radiation phase contrast imaging apparatus according to one aspect of the present invention, with the aforementioned configuration, the object stage can be moved by the moving mechanism to the X-ray source side of the first grating and the second grating side of the first grating. As a result, as compared with the configuration in which the position of the object stage is changed only on the X-ray source side of the first grating, the range in which the object stage can be moved in the optical axis direction can be extended to the second grating side in addition to the X-ray source side of the first grating. Since the level of contrast in the phase contrast image depends on the distance of the object from the first grating, in cases where the object stage can be moved to both the X-ray source side and the second grating side with respect to the first grating, it is possible to secure a range having the same level of contrast on both the X-ray source side of the first grating and the second grating side of the first grating. As a result, it is possible to extend the variable range of the scaling ratio of the object while securing the visibility in the phase contrast image.

In the radiation phase contrast imaging apparatus according to the aforementioned one aspect of the present invention, it is preferably configured such that when moving the object stage across the first grating in the optical axis direction of the X-ray, at least one of the object stage and the first grating is retracted in a direction different from the optical axis direction up to a noninterference position at which the object and the first grating do not interfere in the optical axis direction.

With this configuration, it is possible to suppress the interference between the object and the first grating when moving the object stage across the first grating in the optical axis direction of the X-ray.

In this case, it is preferably configured such that a direction in which the object stage is supported and a direction in which the first grating is supported are different from each other.

Here, in cases where the object stage and the first grating are supported from the same direction, the object stage or the first grating cannot be retraced to a noninterference position unless the structure supporting the object stage and the structure supporting the first grating are moved in mutually orthogonal directions.

On the other hand, in cases where the object stage and the first grating are supported from different directions, even if the structure supporting the object stage and the structure supporting the first grating are moved in directions away from each other in addition to the direction in which the structure supporting the object stage and the structure supporting the first grating are orthogonal with each other, the object stage or the first grating can be moved to a noninterference position. Therefore, by supporting the object stage and the first grating from different directions, as compared with the case in which the object stage and the first grating are supported from the same direction, it is possible to receive less restrictions on the arrangement for preventing interference between the structure supporting the object stage and the structure supporting the first grating.

Also, in the case of moving the structure supporting the object stage and the structure supporting the first grating so as to be away from each other, it is possible to retract the object stage and the first grating in the respective supported directions, which results in a simple device configuration. As a result, it is possible to easily suppress the interference between the object and the first grating, as compared with the case in which the object stage and the first grating are supported from the same direction.

In the configuration in which at least one of the object stage and the first grating is retracted to the noninterference position, it is preferably configured such that the moving mechanism is configured to retract the object stage in a direction different from the optical axis direction and move the object stage across the first grating in the optical axis direction.

With this configuration, with one moving mechanism, the object stage can be retracted to the noninterference position and also can be moved in the optical axis direction across the first grating. As a result, with a less number of parts, a device configuration for moving the object stage across the first grating in the optical axis direction of the X-ray (simplification of the moving mechanism) can be realized without causing interference between the object and the first grating.

In the configuration in which at least one of the object stage and the first grating is retracted to the noninterference position, it is preferably configured such that the imaging apparatus further includes a retraction mechanism configured to retract the first grating in a direction different from the optical axis direction, wherein the moving mechanism is configured to move the object stage across the first grating in the optical axis direction in a state in which the first grating is retracted to the noninterference position by the retraction mechanism.

With such a configuration, it is possible that the retraction mechanism and the moving mechanism can be simplified in configuration specialized for the function to retract the first grating to the noninterference position and the function to move the object stage in the optical axis direction. As a result, while suppressing the complication of the apparatus configuration, a device configuration for moving the object stage across the first grating in the optical axis direction of the X-ray (simplification of the moving mechanism) can be realized without causing interference between the object and the first grating.

In the configuration including the retraction mechanism, it is preferably configured to further include a position detection unit configured to detect a position of the object, wherein the moving mechanism is configured to move the object stage to a position other than a return position of the first grating retraced by the retraction mechanism based on the position of the object detected by the position detection unit.

With this configuration, it is possible to prevent the first grating retracted by the retraction mechanism from coming into contact with the object when returning the first grating to the imaging position.

In the radiation phase contrast imaging apparatus according to the aforementioned one aspect, it is preferably configured such that the moving mechanism is configured to move the object stage to a first range on the X-ray source side of the first grating and a second range in which a distance from the first grating is substantially equal to that of the first range on the second grating side of the first grating.

With this configuration, the position in which the contrast in the phase contrast image becomes substantially equal to each other due to substantially the same distance from the first grating can be included in both the first range and the second range. As a result, it is possible to assuredly generate a phase contrast image changed in the scaling ratio without substantially changing the contrast.

In the radiation phase contrast imaging apparatus according to the aforementioned one aspect of the present invention, it is preferably configured to further include a third grating arranged between the X-ray source and the first grating for enhancing coherence of the X-ray irradiated from the X-ray source, wherein the moving mechanism is configured to move the object stage in the optical axis direction within a range from the first grating to the third grating and within a range from the first grating to the second grating.

With this configuration, in the configuration in which the third grating is included, the range in which the object stage can be moved can be maximized between the third grating and the second grating. As a result, it is possible to maximize the variable width of the scaling ratio of the object in the phase contrast image in the configuration in which the third grating is included.

DESCRIPTION OF PREFERRED EMBODIMENTS

Hereinafter, some embodiments of the present invention will be described with reference to the drawings.

First Embodiment

Figure 1:
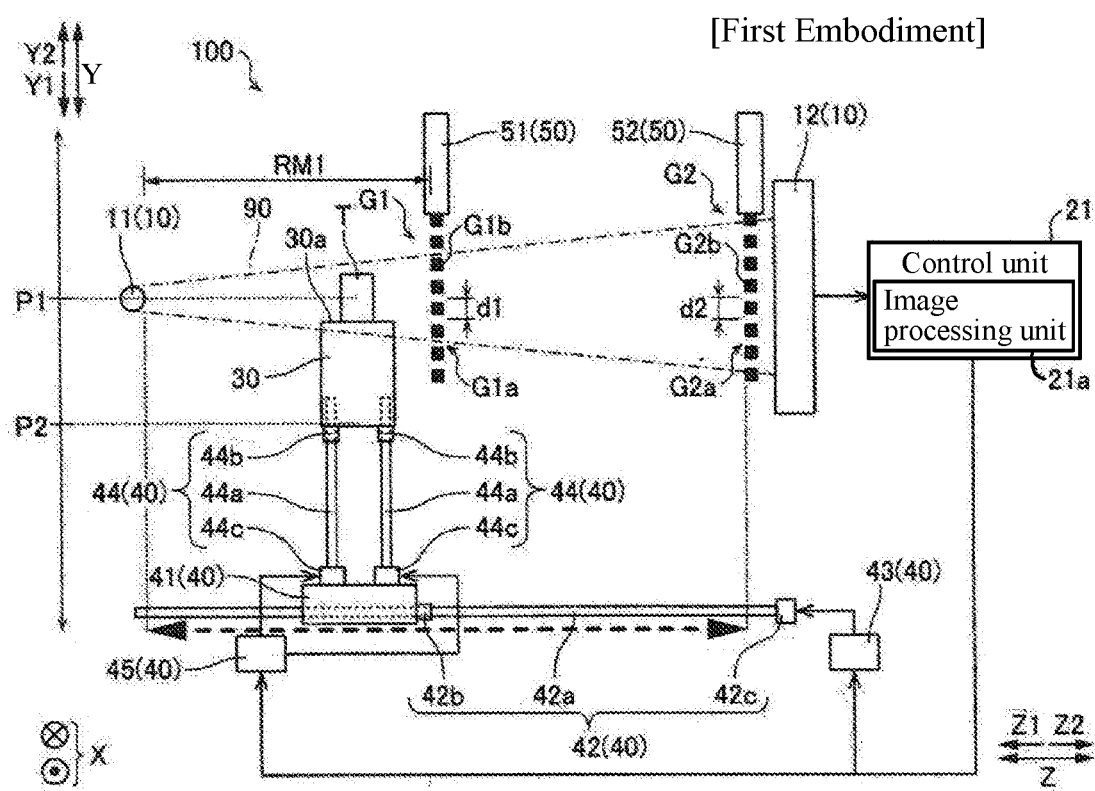
FIG. 1 is a schematic diagram showing an overall configuration of a radiation phase contrast imaging apparatus according to a first embodiment of the present invention.

With reference to FIG. 1, a configuration of an X-ray phase imaging apparatus 100 according to a first embodiment of the present invention will be described. Note that the X-ray phase imaging apparatus 100 is an example of the "radiation phase contrast imaging apparatus" recited in claims.

(Configuration of X-Ray Phase Imaging Apparatus)

The X-ray phase imaging apparatus 100 is, as shown in FIG. 1, provided with an image signal generation system 10 including an X-ray source 11 and an image signal detector 12, a plurality of gratings including a first grating G1 and a second grating G2, a control unit 21, an object stage 30, a moving mechanism 40, and a grating holder 50.

In the X-ray phase imaging apparatus 100, the X-ray source 11, the first grating G1, the second grating G2, and the image signal detector 12 are arranged in this order in the irradiation axis direction (optical axis direction, Z-direction) of the X-ray. That is, the first grating G1 and the second grating G2 are arranged between the X-ray source 11 and the image signal detector 12. Note that in this specification, the horizontal direction and the vertical direction orthogonal to the optical axis direction of the X-ray are denoted as the X-direction and the Y-direction, respectively.

The X-ray source 11 is configured to generate X-rays when a high voltage is applied. The X-ray source 11 is configured to irradiate the generated X-ray with a microfocus.

The first grating G1 is a diffraction grating (phase grating), which changes the phase of the passing X-ray. The first grating G1 is provided with a slit G1a and an X-ray absorption portion G1b arranged with a predetermined period (grating pitch) d1 in the Y-direction. The slit G1a and the X-ray absorption portion G1b are each formed so as to extend in the X-direction.

The first grating G1 is arranged between the X-ray source 11 and the second grating G2 so as to form a self-image (by a Talbot effect) by the X-ray irradiated from the X-ray source 11. The Talbot effects means that when an X-ray having coherence passes through a grating in which slits are formed, a grating image (self-image) is formed at a position away from the grating by a predetermined distance (a Talbot distance).

The second grating G2 is provided with a plurality of slits G2a and X-ray absorption portions G2b arranged in the Y-direction at a predetermined period (grating pitch) d2. The slit G2a and the X-ray absorption portion G2b are each formed so as to extend in the X-direction.

The second grating G2 is arranged between the first grating G1 and the image signal detector 12 to cause interference with the self-image formed by the first grating G1. The second grating G2 is arranged at a position separated from the first grating G1 by a Talbot distance to cause interference between the self-image and the second grating G2.

The image signal detector 12 is configured to detect the X-ray irradiated from the X-ray source 11 and converts the detected X-ray into an electric signal. The image signal detector 12 is, for example, an FPD (Flat Panel Detector). The image signal detector 12 is composed of a plurality of conversion elements (not shown) and a plurality of pixel electrodes (not shown) arranged on the plurality of conversion elements. The plurality of conversion elements and pixel electrodes are arranged in the X-direction and the Y-direction at a predetermined period (pixel pitch). The detection signal (image signal) of the image signal detector 12 is sent to the image processing unit 21a of the control unit 21.

The control unit 21 is provided with the image processing unit 21a capable of generating an X-ray image. Further, the control unit 21 is configured to control the operation of the moving mechanism 40. The control unit 21 includes, for example, a CPU (Central Processing Unit), a ROM (Read Only Memory), a RAM (Random Access Memory), and the like.

The image processing unit 21a is configured to generate a phase contrast image based on the detection signal sent from the image signal detector 12. The image processing unit 21a includes processors, such as, e.g., a GPU (Graphics Processing Unit) and an FPGA (Field-Programmable Gate Array) configured for image processing.

The phase contrast image is a generic name of images captured using the first grating G1 and the second grating G2 and includes at least one of an absorption image, a phase differential image, and a dark field image, for example. The absorption image denotes an X-ray image imaged based on the difference of the X-ray absorption degree due to the object T. The phase differential image denotes an X-ray image imaged based on the phase shift of the X-ray. The dark field image denotes a visibility image obtained by a visibility change based on small-angle scattering by an object. Further, the dark field image is also called a small-angle scattering image. The "visibility" denotes sharpness.

The phase contrast image is generated based on the X-ray signal intensity change curve when at least one of the first grating G1 and the second grating G2 is translated in the grating pitch direction (Y-direction). Specifically, the phase differential image is generated by imaging the magnitude of the phase shift of the signal intensity change curve of the X-ray when the object T is arranged with respect to the signal intensity change curve of the X-ray when the object T is not arranged by utilizing the refraction of the X-ray that has passed through the object T.

The absorption image is generated by imaging the difference of the detection intensity of the X-ray (included in the signal intensity change curve) when the object T is arranged with respect to the detection intensity of the X-ray (included in signal intensity change curve) when the object T is not arranged.

The dark field image is generated by imaging the magnitude of the decrease amount (crush amount) of the amplitude of the signal intensity change curve of the X-ray when the object T is arranged with respect to the amplitude of the signal intensity change curve of the X-ray when the object T is not arranged.

The object stage 30 has a placement surface 30a capable of holding the object T. The object stage 30 may have a holding mechanism of the object stage 30, such as, e.g., a chuck mechanism (not shown) and a hand mechanism (not shown). In addition, the object stage 30 is configured to be supported by the moving mechanism 40 from the lower side (Y1-direction) of the vertical direction orthogonal to the optical axis direction.

The moving mechanism 40 is configured to move the object stage 30 in the optical axis direction (Z-direction). The moving mechanism 40 is provided with a movable base 41, a linear motion mechanism 42, and a drive unit 43.

The movable base 41 is arranged below the object stage 30 and is configured to support the object stage 30. That is, the movable base 41 is configured to move in the optical axis direction together with the object stage 30. Note that the movable base 41 is configured to be movable between the X-ray source 11 and the second grating G2 in the optical axis direction.

The linear motion mechanism 42 is a linear motion mechanism for moving the movable base 41 together with the object stage 30 in the optical axis direction. The linear motion mechanism 42 includes a shaft unit 42a, a movable unit 42b, and a power input unit 42c.

The linear motion mechanism 42 is a ball screw mechanism. That is, the shaft unit 42a is composed of a ball screw shaft extending in the optical axis direction, and is configured to move the movable unit 42b in the optical axis direction. The movable unit 42b is a ball nut screwed onto the shaft unit 42a and is fixed to the movable base 41. The power input unit 42c transmits the power input from the drive unit 43 to the shaft unit 42a to rotate the shaft unit 42a.

The drive unit 43 is configured to input power to the power input unit 42c directly or via a drive transmission unit (not shown). The drive unit 43 is, for example, a motor, such as, e.g., a servomotor and a stepping motor. The operation of the drive unit 43 is controlled by the control unit 21.

The grating holder 50 includes a grating holder 51 for holding a first grating G1 and a grating holder 52 for holding a second grating G2. The first grating G1 and the second grating G2 are respectively configured to be supported by the grating holder 51 and the grating holder 52 from the upper side (Y2-direction) in the vertical direction orthogonal to the optical axis direction. That is, in the first embodiment, the direction (Y1-direction) in which the object stage 30 is supported and the direction (Y2-direction) in which the first grating G1 is supported are configured to be different from each other.

With the aforementioned configuration, in the X-ray phase imaging apparatus 100, the object stage 30 holding the object T can be moved in the optical axis direction at the imaging position P1 (within the irradiation range 90 of the X-ray) within the range RM1 between the X-ray source 11 and the first grating G1 by the moving mechanism 40.

(Configuration for Moving Object Stage Across First Grating in Optical Axis Direction)

Here, in the first embodiment, the object stage 30 is configured to be movable in the optical axis direction across the first grating G1. When the object stage 30 is moved in the optical axis direction between the X-ray source 11 and the first grating G1, it is necessary to avoid that the object T and the object stage 30 interferes with the X-ray source 11 or the first grating G1.

Therefore, with reference to FIG. 1, the configuration for moving the object stage 30 across the first grating G1 in the optical axis direction (Z-direction) will be described.

As shown in FIG. 1, the moving mechanism 40 is further provided with a linear motion mechanism 44 and a drive unit 45.

The linear motion mechanism 44 is a linear motion mechanism (lifting mechanism) for moving the object stage 30 in a vertical direction (Y-direction) orthogonal to the optical axis direction. The linear motion mechanism 44 includes a shaft unit 44a, a movable unit 44b, and a power input unit 44c.

The linear motion mechanism 44 is a ball screw mechanism in the same manner as in the linear motion mechanism 42. That is, the shaft unit 44a is composed of a ball screw shaft extending in the vertical direction, and is configured to move the movable unit 44b in the vertical direction. The movable unit 44b is a ball nut screwed onto the shaft unit 44a and is fixed to the object stage 30. The power input unit 44c is fixed to the movable base 41, and transmits the power input from the drive unit 45 to the shaft unit 44a to rotate the shaft unit 44a.

The drive unit 45 is configured to input power to the power input unit 44c directly or via a drive transmission unit (not shown). The drive unit 45 is, for example, a motor, such as, e.g., a servomotor and a stepping motor. The operation of the drive unit 45 is controlled by the control unit 21.

With the aforementioned configuration, in the X-ray phase imaging apparatus 100, it is possible to move the object stage 30 in the vertical direction (Y-direction) orthogonal to the optical axis direction by the moving mechanism 40. Further, the moving mechanism 40 is configured to move the object stage 30 from the imaging position P1 in the Y1-direction to a position where the object T and the object stage 30 do not overlap with the first grating G1 as seen from the optical axis direction.

That is, in the first embodiment, the X-ray phase imaging apparatus 100 is configured to retract the object stage 30 in a direction (Y1-direction) different from the optical axis direction up to the noninterference position P2 where the object T and the first grating G1 do not interfere in the optical axis direction when moving the object stage 30 across the first grating G1 in the optical axis direction (Z-direction) of the X-ray.

(Movement of Object Stage Across First Grating in Optical Axis Direction)

Next, with reference to FIG. 2 to FIG. 4, the operation of moving the object stage 30 across the first grating G1 in the optical axis direction will be described. It is assumed that the current position of the object T is in the imaging position P1 as shown in FIG. 1. It is also assumed that the current position of the object T is between the X-ray source 11 and the first grating G1 in the Z-direction as shown in FIG. 1.

Figure 2:
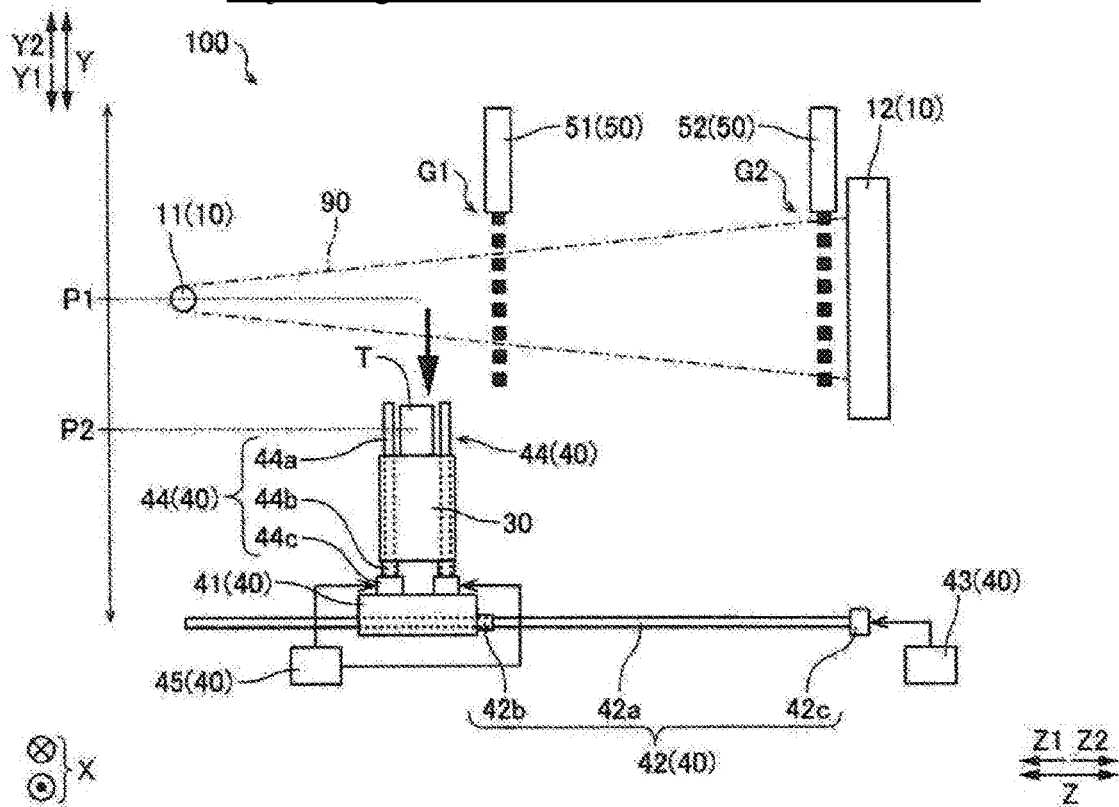
FIG. 2 is a diagram showing a state in which an object stage is retracted to a noninterference position in the radiation phase contrast imaging apparatus according to the first embodiment.

First, as shown in FIG. 2, the control unit 21 controls the moving mechanism 40 to retract the object T and the object stage 30 in the imaging position P1 to the noninterference position P2. Specifically, the control unit 21 drives the drive unit 45 to move the object stage 30 holding the object T by the linear motion mechanism 44 in the Y1-direction by a predetermined distance (distance between P1 and P2) (which is necessary for retracting the object T to the noninterference position P2).

Figure 3:
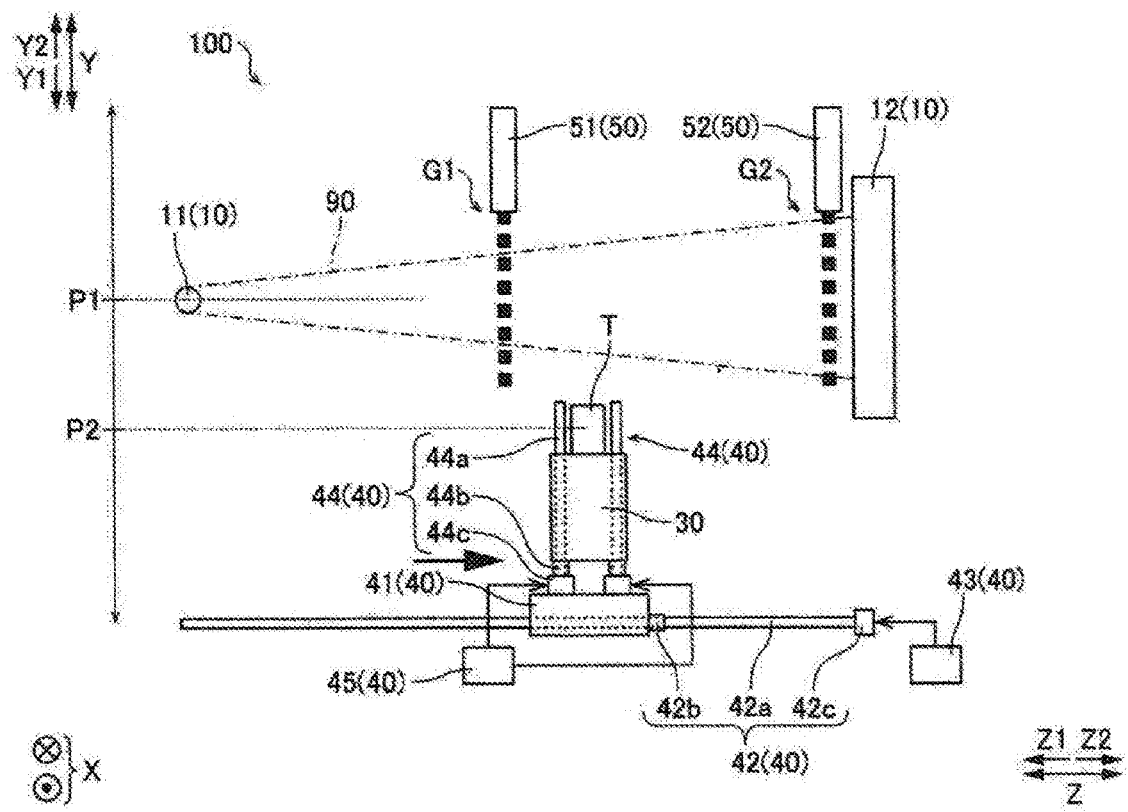
FIG. 3 is a diagram showing a state of moving the object stage retracted to the noninterference position across the first grating in the optical axis direction in the radiation phase contrast imaging apparatus according to the first embodiment.

Next, as shown in FIG. 3, the control unit 21 controls the moving mechanism 40 to move the object T and the object stage 30 across the first grating G1 in the optical axis direction in a state in which the object T is in the noninterference position P2. Specifically, the control unit 21 drives the drive unit 43 to move the object stage 30 holding the object T in the Z2-direction by the linear motion mechanism 42 by a predetermined distance (necessary for moving the object T across the first grating G1 in the optical axis direction).

Figure 4:
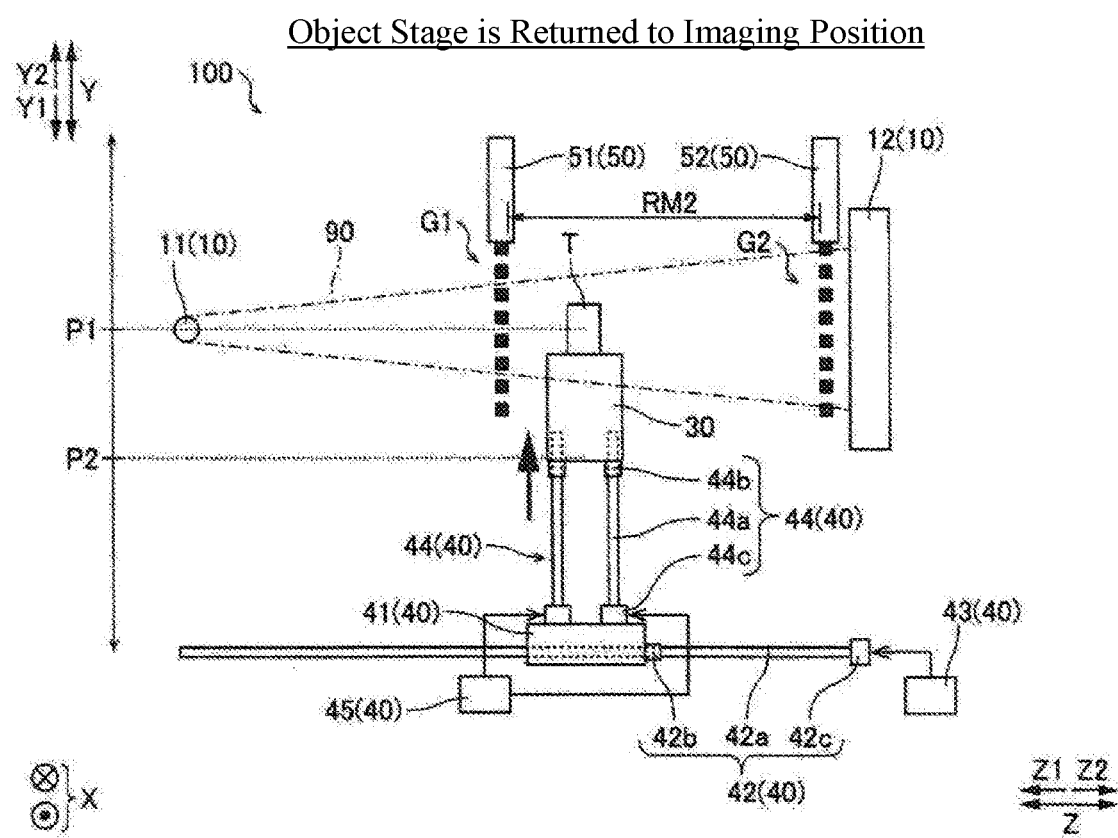
FIG. 4 is a diagram showing a state of returning the object stage moved in the optical axis direction across the first grating to the imaging position in the radiation phase contrast imaging apparatus according to the first embodiment.

Then, as shown in FIG. 4, the control unit 21 controls the moving mechanism 40 to restore the object T in the noninterference position P2 between the first grating G1 and the second grating G2 to the imaging position P1. Specifically, the control unit 21 drives the drive unit 45 to move the object stage 30 holding the object T by the linear motion mechanism 44 in the Y2-direction by a predetermined distance (distance between P2 and P1) (which is necessary for restoring the object T to the imaging position P1).

As described above, in the first embodiment, the moving mechanism 40 is configured to retract the object stage 30 to the noninterference position P2 in the direction (Y1-direction) different from the optical axis direction (Z-direction) and move the object stage 30 across the first grating G1 in the optical axis direction (Z-direction).

Therefore, in the X-ray phase imaging apparatus 100, the object stage 30 holding the object T can be moved by the moving mechanism 40 in the optical axis direction within the range RM2 between the first grating G1 and the second grating G2 (see FIG. 4) in addition to the range RM1 between the X-ray source 11 and the first grating G1.

It should be noted that the distance between the X-ray source 11 and the first grating G1 and the distance between the first grating G1 and the second grating G2 depend on the grating pitch d1 of the first grating G1 and the grating pitch d2 of the second grating G2. Therefore, the magnitude of the range RM1 and that of the range RM2 are not necessarily substantially equal as depicted in the figure.

(Relationship Between Position of Object and Scaling Ratio of Phase Contrast Image)

Next, with reference to FIG. 5 and FIG. 8, the relationship between the position of the object T between the X-ray source 11 and the image signal detector 12 and the scaling ratio of the phase contrast image will be described.

Figure 5A:
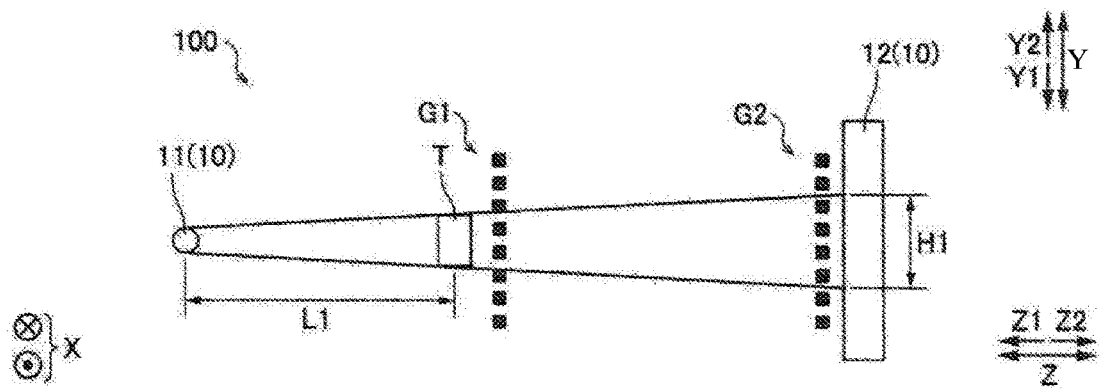
FIG. 5A is a diagram for explaining the relationship between the position of the object and the scaling ratio of the phase contrast image.
Figure 5B:
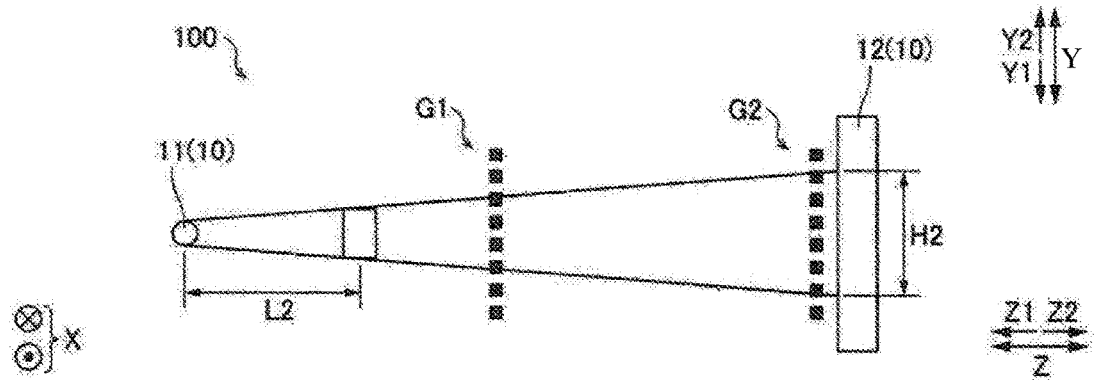
FIG. 5B is another diagram for explaining the relationship between the position of the object and the scaling ratio of the phase contrast image.

As shown in FIG. 5A, when the object T is arranged at a position of a distance L1 from the X-ray source 11, the size of the object T in the Y-direction detected by the image signal detector 12 is H1. On the other hand, as shown in FIG. 5B, when the object T is arranged at the position of the distance L2 (shorter than the distance L1) from the X-ray source 11, the size of the object T (in the Y-direction) detected by the image signal detector 12 is H2 (larger than H1).

That is, by bringing the object T closer to the X-ray source 11 side (Z1 side), the object T in the phase contrast image can be enlarged. By bringing the object T closer to the image signal detector 12 side (Z2 side), the object T in the phase contrast image can be reduced.

Figure 8A:
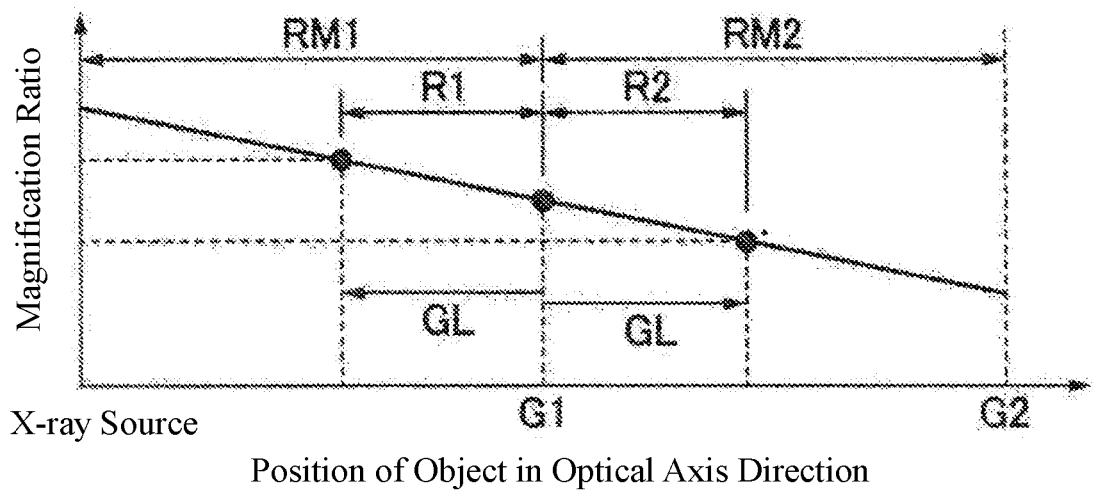
FIG. 8A is a diagram for explaining the relationship between the scaling ratio of the phase contrast image and the contrast in the phase contrast image.

Although FIG. 5 does not show an example in which the object T is arranged between the first grating G1 and the second grating G2, the property concerning the enlargement and reduction of the object T is the same as in the case in which the object T is arranged between the X-ray source 11 and the first grating G1. Therefore, as shown in FIG. 8A, in the X-ray phase imaging apparatus 100, the magnification ratio in the phase contrast image has a negative correlation with the distance from the X-ray source 11 to the object T in the optical axis direction.

(Relationship Between Position of Object and Contrast in Phase Contrast Image)

Next, with reference to FIG. 6 to FIG. 8, the relationship between the position of the object T between the X-ray source 11 and the image signal detector 12 and the contrast in the phase contrast image will be described.

Figure 6A:
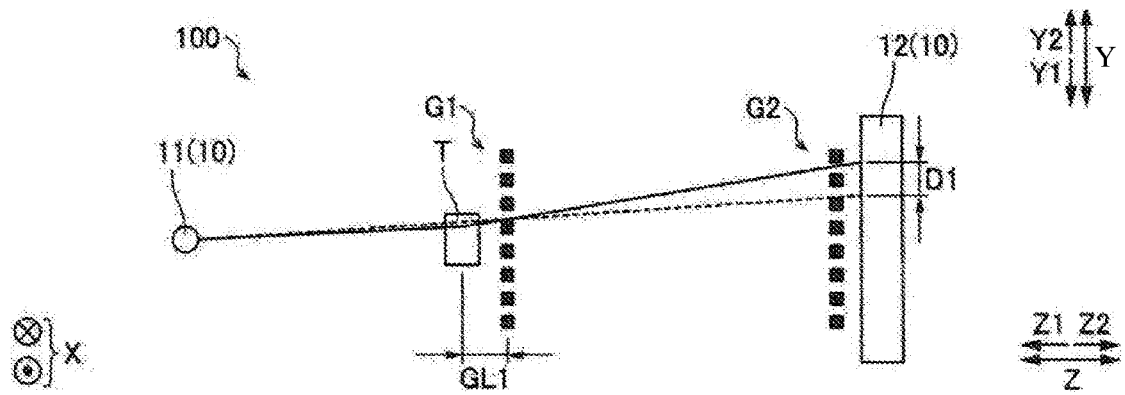
FIG. 6A is a diagram for explaining the relationship between the position of the object and the contrast in the phase contrast image when the object is arranged on the X-ray source side of the first grating.
Figure 6B:
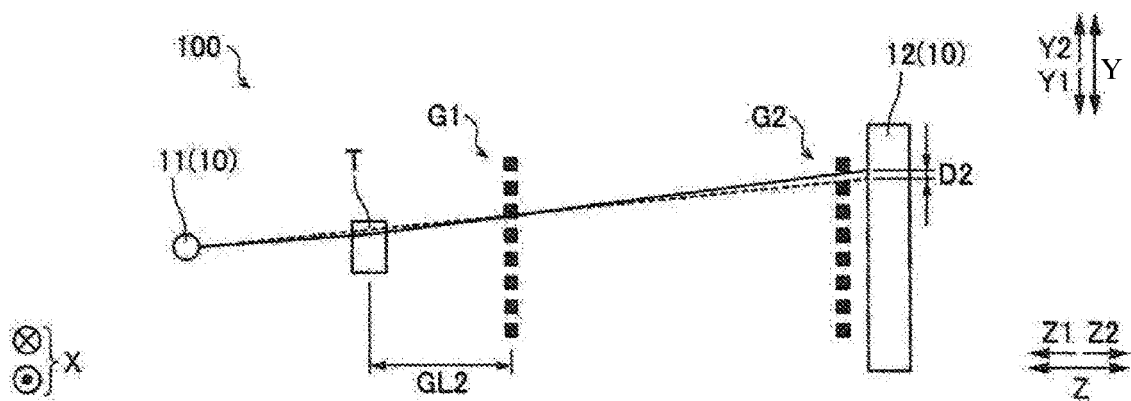
FIG. 6B is another diagram for explaining the relationship between the position of the object and the contrast in the phase contrast image when the object is arranged on the X-ray source side of the first grating.
Figure 7A:
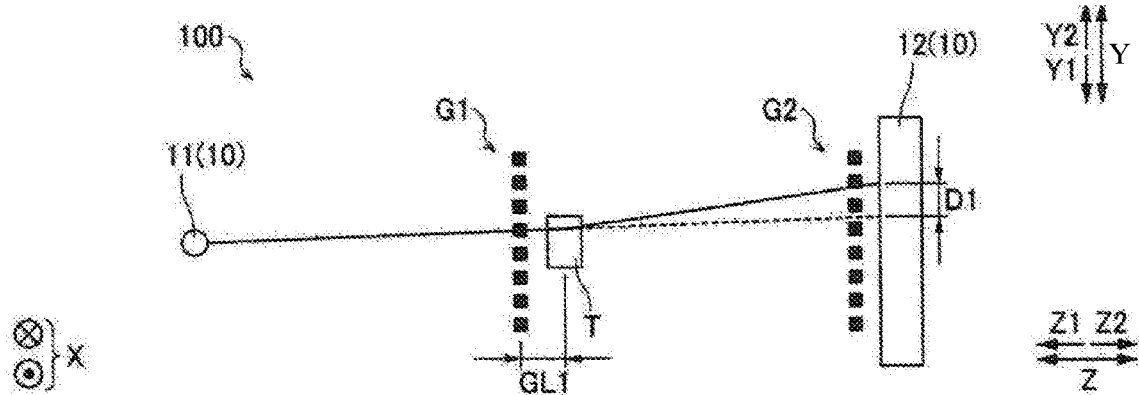
FIG. 7A is a diagram for explaining the relationship between the position of the object and the contrast in the phase contrast image when the object is arranged on the second grating side of the first grating.
Figure 7B:
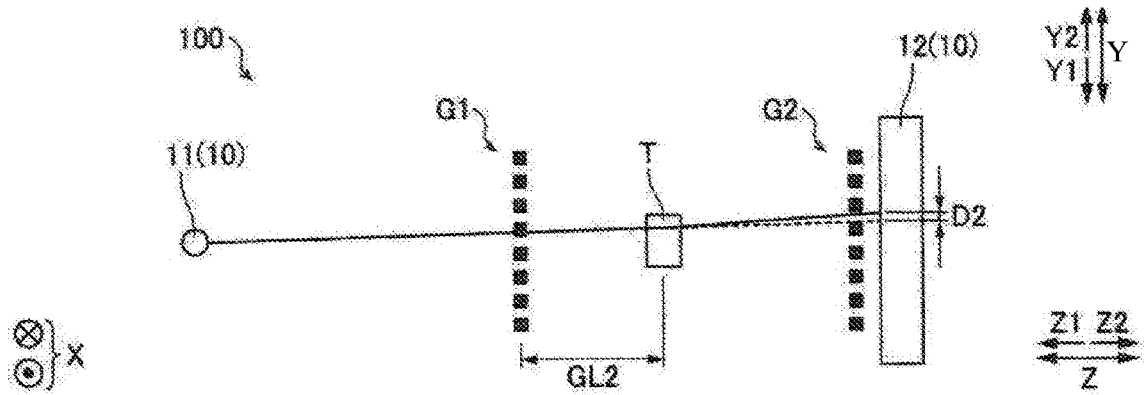
FIG. 7B is another diagram for explaining the relationship between the position of the object and the contrast in the phase contrast image when the object is arranged on the second grating side of the first grating.

In FIG. 6A and FIG. 6B, a case in which the object T is arranged between the X-ray source 11 and the first grating G1 is shown. In FIG. 7A and FIG. 7B, the case in which the object T is arranged between the first grating G1 and the second grating G2 is shown. In FIG. 6A, FIG. 6B, FIG. 7A, and FIG. 7B, the X-ray in the case where the object T is arranged is indicated by a solid line and the X-ray in the case where the object T is not arranged is indicated by a chain line. Also, in FIG. 6A, FIG. 6B, FIG. 7A, and FIG. 7B, the case in which an X-ray (solid line) irradiated to the same position of the object T is refracted at a predetermined angle is shown.

As shown in FIG. 6A, when the object T is arranged at the position of the distance GL1 from the first grating G1 to the X-ray source 11 side (the Z1 side) between the case in which the object T is arranged and the case in which the object T is not arranged, the position to which the X-ray having passed through the first grating G1 reaches is shifted by the shift amount D1. Further, as shown in FIG. 6B, when the object T is arranged at the position of the distance GL2 (larger than GL1) from the first grating G1 to the X-ray source 11 side (the Z1 side), between the case in which the object T is arranged and the case in which the object T is not arranged, the position to which the X-ray having passed through the first grating G1 reaches is shifted by the shift amount D2 (smaller than the shift amount D0.

As shown in FIG. 7A, when the object T is arranged at the position of the distance GL1 from the first grating G1 to the second grating G2 side (the Z2 side), between the case in which the object T is arranged and the case in which the object T is not arranged, the position to which the X-ray having passed through the first grating G1 reaches is shifted by the shift amount D1. Further, as shown in FIG. 7B, when the object T is arranged at the position of the distance GL2 from the first grating G1 to the second grating G2 side (the Z2 side), between the case in which the object T is arranged and the case in which the object T is not arranged, the position to which the X-ray having passed through the first grating G1 reaches is shifted by the shift amount D2.

That is, even in cases where the object T is arranged on the X-ray source 11 side or the second grating G2 side, by moving the object T closer to the first grating G1 (decreasing the distance between the object T and the first grating G1), the phase shift of the X-ray due to the object T increases. Further, by moving the object T away from the first grating G1 (increasing the distance between the object T and the first grating G1), the phase shift of the X-ray due to the object T decreases. Therefore, as shown in FIG. 8B, the magnitude of the phase shift of the X-ray (contrast in the phase contrast image) has a negative correlation with the distance of the object T from the first grating G1.

(Relationship Between Scaling Ratio of Phase Contrast Image and Contrast in Phase Contrast Image)

Figure 8B:
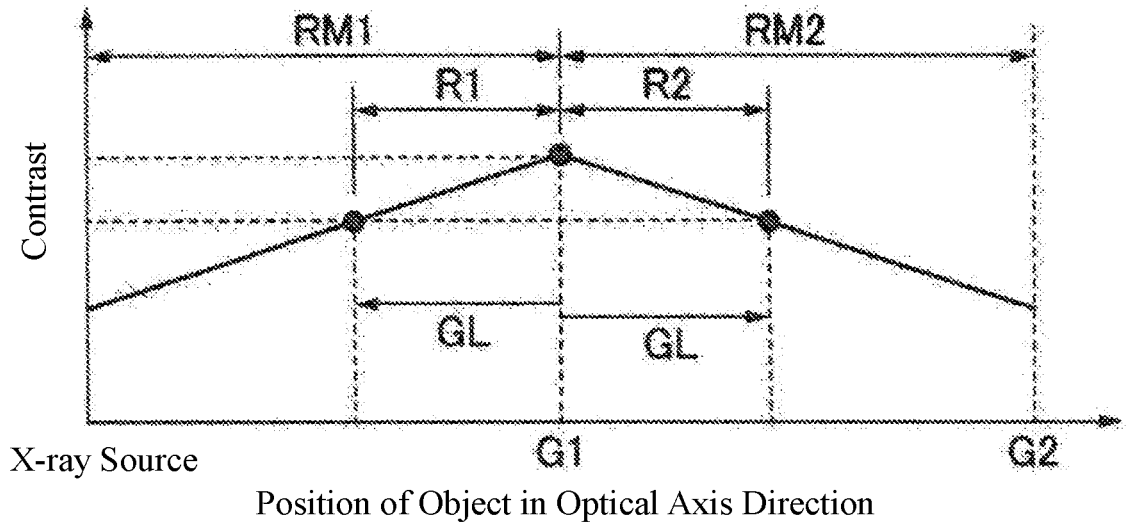
FIG. 8B is another diagram for explaining the relationship between the scaling ratio of the phase contrast image and the contrast in the phase contrast image.

As shown in FIG. 8B, the contrast in the phase contrast image has a negative correlation between the X-ray source 11 side of the first grating G1 and the second grating G2 side of the first grating G1 at the same ratio as the distance from the first grating G1. In particular, the contrast when the object T is arranged at the position of the distance GL from the first grating G1 on the X-ray source 11 side of the first grating G1 is approximately the same as the contrast when the object T is arranged at the position of the distance GL from the first grating G1 on the second grating G2 side of the first grating G1.

Here, in the X-ray phase imaging apparatus 100, as described above, it is possible to move the object T in the optical axis direction at the imaging position P1 within the range RM1 between the X-ray source 11 and the first grating G1 and the range RM2 between the first grating G1 and the second grating G2. Therefore, in the first embodiment, within the range of the range RM1 and that of the range RM2, the object stage 30 can be moved to the first range R1 on the X ray source 11 side of the first grating G1 and the second range R2 in which the distance GL from the first grating G1 is equal to the first range R1 on the second grating G2 side of the first grating G1.

As a result, the position at which the contrasts in the phase contrast image become substantially equal to each other due to the equal distance GL from the first grating G1 is included in both the X-ray source 11 side of the first grating G1 and the second grating G2 side of the first grating G1. That is, in the X-ray phase imaging apparatus 100, it is possible to capture the image of the object T at two positions where the distances GL from the first grating G1 become equal to each other within the range of the range RM1 and that of the range RM2. As a result, the X-ray phase imaging apparatus 100 can capture X-ray images of two kinds of magnification ratios with substantially equal contrast. Further, in the X-ray phase imaging apparatus 100, as shown in FIG. 8, it is possible to change the magnification ratio in the range of in the range of 2×GL within the fluctuation range of the contrast corresponding to the distance GL.

The width of the first range R1 and that of the second range R2 are determined by the distance GL from the first grating G1 dependent on the contrast of the object T. Also, the width of the first range R1 and that of the second range R2 each do not exceed the range RM1 and the range RM2.

Effects of First Embodiment

In the first embodiment, the following effects can be obtained.

In the first embodiment, as described above, the X-ray phase imaging apparatus 100 includes the moving mechanism 40 that moves the object stage 30 holding the object T. The moving mechanism 40 can move the object stage 30 to the X-ray source 11 side (Z1 side) of the first grating G1 and the second grating G2 side (Z2 side) of the first grating G1. As a result, as compared with the configuration in which the position of the object stage 30 is changed only on the X-ray source 11 side of the first grating G1, the range in which the object stage 30 can be moved in the optical axis direction (Z-axis direction) can be extended to the second grating G2 side of the first grating G1 in addition to the X-ray source 11 side of the first grating G1.

The level of contrast in the phase contrast image depends on the distance of the object T from the first grating G1. Therefore, in cases where the object stage 30 can be moved to both the X-ray source 11 side and the second grating G2 side with respect to the first grating G1, it is possible to secure a range having the same level of contrast on both the X-ray source 11 side of the first grating G1 and the second grating G2 side of the first grating G1. As a result, it is possible to extend the variable range of the scaling ratio of the object T while securing the visibility in the phase contrast image.

Further, in the first embodiment, as described above, the X-ray phase imaging apparatus 100 is configured to retract the object stage 30 in a direction (Y1-direction) different from the optical axis direction up to the noninterference position P2 where the object T and the first grating G1 do not interfere in the optical axis direction when moving the object stage 30 across the first grating G1 in the optical axis direction (Z-direction) of the X-ray. With this configuration, it is possible to suppress the interference between the object T and the first grating G1 when moving the object stage 30 across the first grating G1 in the optical axis direction of the X-ray.

Further, in the first embodiment, as described above, in the X-ray phase imaging apparatus 100, the direction in which the object stage 30 is supported (Y1-direction) and the direction in which the first grating G1 is supported (Y2-direction) are configured to be different from each other. With this, by supporting the object stage 30 and the first grating G1 from different directions, as compared with the case in which the object stage 30 and the first grating G1 are supported from the same direction, there is less restrictions on the arrangement for preventing the interference between the structure (moving mechanism 40) supporting the object stage 30 and the structure (grating holder 51) supporting the first grating G1.

Further, by moving the structure supporting the object stage 30 and the structure supporting the first grating G1 so as to be away from each other, it is possible to retract the object stage 30 and the first grating G1 in the supported direction, respectively, which results in a simple device configuration. As a result, it is possible to easily suppress the interference between the object T and the first grating G1, as compared with the case in which the object stage 30 and the first grating G1 are supported from the same direction.

Further, in the first embodiment, as described above, in the X-ray phase imaging apparatus 100, the moving mechanism 40 is configured to retract the object stage 30 in the direction (Y1-direction) different from the optical axis direction (Z-direction) and move the object stage 30 across the first grating G1 in the optical axis direction. With this configuration, with one moving mechanism 40, the object stage 30 can be retracted to the noninterference position P2 and also can be moved in the optical axis direction across the first grating G1. As a result, with a lesser number of parts, a device configuration (simplification of the moving mechanism 40) for moving the object stage 30 across the first grating G1 in the optical axis direction of the X-ray can be realized without causing interference between the object T and the first grating G1.

Further, in the first embodiment, as described above, in the X-ray phase imaging apparatus 100, the moving mechanism 40 is configured so as to move the object stage 30 to the first range R1 on the X-ray source 11 side of the first grating G1 and the second range R2 in which the distance GL from the first grating G1 is equal to the first range R1 on the second grating G2 side of the first grating G1.

With this configuration, the position in which the contrasts in the phase contrast image become substantially equal to each other due to the same distance GL from the first grating G1 can be included in both the first range R1 and the second range R2. As a result, it is possible to assuredly generate a phase contrast image in which the scaling ratio is changed without changing the contrast.

Second Embodiment

Next, a second embodiment will be described with reference to FIG. 9 to FIG. 12. In the second embodiment, unlike the X-ray phase imaging apparatus 100 of the aforementioned first embodiment equipped with the moving mechanism 40 that performs both the movement in the optical axis direction (Z-direction) and the retraction to the noninterference position P2 with respect to the object stage 30, an example in which a mechanism for retracting to the noninterference position P3 is provided separately from the moving mechanism 240 of the object stage 30. Note that in the figures, the same reference numeral is allotted to the same configuration as in the first embodiment.
(Configuration of X-Ray Phase Imaging Apparatus)

Figure 9:
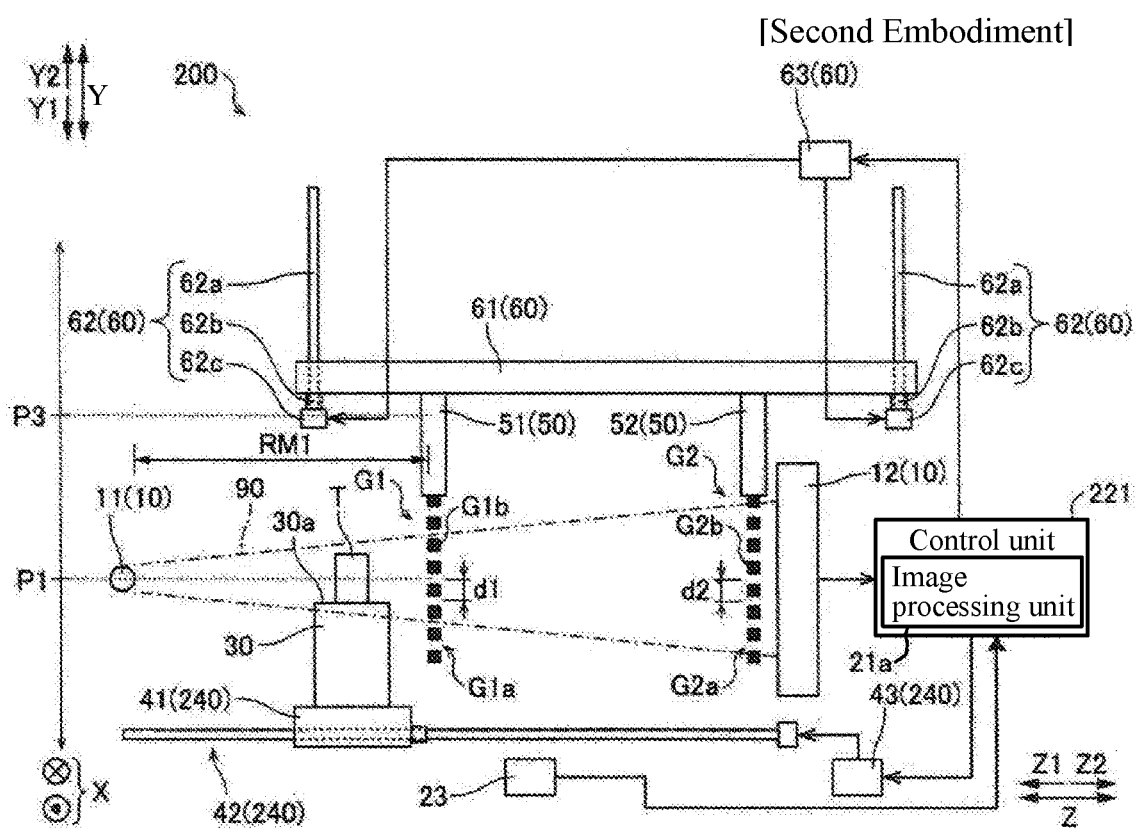
FIG. 9 is a schematic diagram showing an overall configuration of a radiation phase contrast imaging apparatus according to a second embodiment of the present invention.

As shown in FIG. 9, the X-ray phase imaging apparatus 200 according to the second embodiment of the present invention is provided with a moving mechanism 240, a retraction mechanism 60, a control unit 221, and a position detection unit 23. Note that the X-ray phase imaging apparatus 200 is an example of the "radiation phase contrast imaging apparatus" recited in claims.

In the same manner as the moving mechanism 40 of the X-ray phase imaging apparatus 100 of the first embodiment, the moving mechanism 240 is configured to move the object stage 30 in the optical axis direction (Z-direction). On the other hand, different from the moving mechanism 40 of the X-ray phase imaging apparatus 100 of the first embodiment, the moving mechanism 240 does not have a configuration for retracting the object stage 30 to the noninterference position P3. That is, the moving mechanism 240 has a configuration in which the linear motion mechanism 42 and the drive unit 43 are omitted from moving mechanism 40 of the X-ray phase imaging apparatus 100 of the first embodiment.

The retraction mechanism 60 is a configuration for retracting the first grating G1 to the noninterference position P3. That is, the retraction mechanism 60 is provided to move the object stage 30 across the first grating G1 in the optical axis direction. The retraction mechanism 60 is equipped with a hanging portion 61, a linear motion mechanism 62, and a drive unit 63.

The hanging portion 61 is fixed to the linear motion mechanism 62 and is configured to suspend the first grating G1 and the second grating G2 from the Y2-direction side.

The linear motion mechanism 62 is a linear motion mechanism (lifting mechanism) for moving the first grating G1 and the second grating G2 in a vertical direction (Y-direction) orthogonal to the optical axis direction. The linear motion mechanism 62 includes a shaft unit 62a, a movable unit 62b, and a power input unit 62c.

The linear motion mechanism 62 is a ball screw mechanism in the same manner as the linear motion mechanism 42 and the linear motion mechanism 44 in the X-ray phase imaging apparatus 100 of the first embodiment. That is, the shaft unit 62a is composed of a ball screw shaft extending in the vertical direction, and is configured to move the movable unit 62b in the vertical direction. The movable unit 62b is a ball nut screwed onto the shaft unit 62a and is fixed to the hanging portion 61. The power input unit 62c transmits the power input from the drive unit 63 to the shaft unit 62a to rotate the shaft unit 62a.

The drive unit 63 is configured to input power to the power input unit 62c directly or via a drive transmission unit (not shown). The drive unit 63 is, for example, a motor, such as, e.g., a servomotor and a stepping motor. The operation of the drive unit 63 is controlled by the control unit 221.

The control unit 221 is configured to control the operation of the moving mechanism 240 and that of the retraction mechanism 60. Further, the control unit 221 is configured to perform control to stop the operation of the retraction mechanism 60 based on the signal sent from the position detection unit 23.

The position detection unit 23 is configured to detect the position of the object T in the optical axis direction. The position detection unit 23 is configured to output a signal for stopping the operation of the retraction mechanism 60 to the control unit 221 when the object T is arranged at the position to be restored when the first grating G1 returns from the noninterference position P3 to the imaging position P1. As a result, the moving mechanism 240 can move the object stage 30 to a position other than the return position of the first grating G1 retracted by the retraction mechanism 60. The position detection unit 23 includes, for example, an optical sensor such as an infrared sensor, an image sensor (camera), and the like.

With the aforementioned configuration, in the X-ray phase imaging apparatus 200, it is possible to move the first grating G1 by the retraction mechanism 60 in the vertical direction (Y-direction) orthogonal to the optical axis direction. Furthermore, the retraction mechanism 60 is configured to move the first grating G1 in the Y2-direction to a position where the first grating G1 does not overlap (overlap) the object T and the object stage 30 as seen from the optical axis direction.

That is, in the second embodiment, the X-ray phase imaging apparatus 200 is configured to retract the first grating G1 in a direction (Y2-direction) different from the optical axis direction up to the noninterference position P3 where the object T and the first grating G1 do not interfere in the optical axis direction when moving the object stage 30 across the first grating G1 in the optical axis direction (Z-direction) of the X-ray.

(Movement of Object Stage Across First Grating in Optical Axis Direction)

Next, with reference to FIG. 10 to FIG. 12, the operation of moving the object stage 30 across the first grating G1 in the optical axis direction will be described. It is assumed that the current position of the object T is in the imaging position P1 as shown in FIG. 9. It is also assumed that the current position of the object T is between the X-ray source 11 and the first grating G1 in the Z-direction as shown in FIG. 9.

Figure 10:
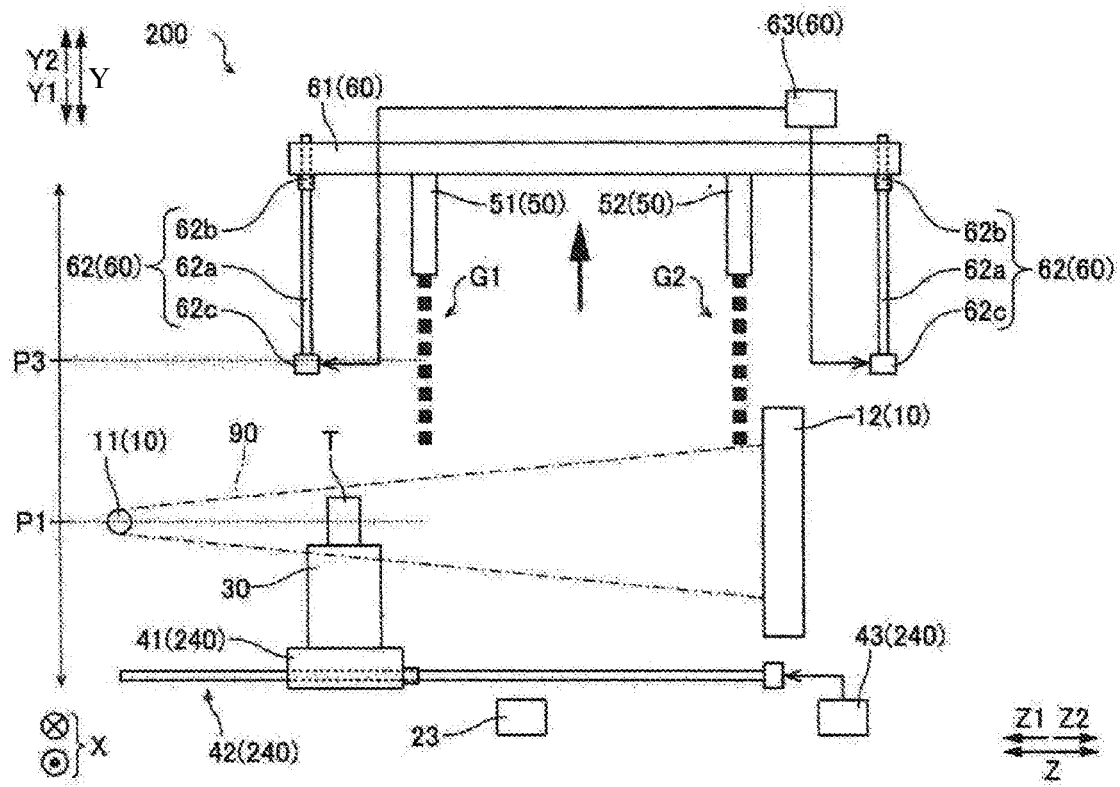
FIG. 10 is a diagram showing a state of retracting a first grating to a noninterference position in the radiation phase contrast imaging apparatus according to the second embodiment.

First, as shown in FIG. 10, the control unit 221 controls the retraction mechanism 60 to retract the first grating G1 positioned in the imaging position P1 to the noninterference position P3. More specifically, the control unit 221 drives the drive unit 63 to move the first grating G1 held by the grating holder 51 in the Y2-direction by a predetermined distance (distance between P1 and P3) (necessary for retracting the first grating G1 to the noninterference position P3) by the linear motion mechanism 62.

Figure 11:
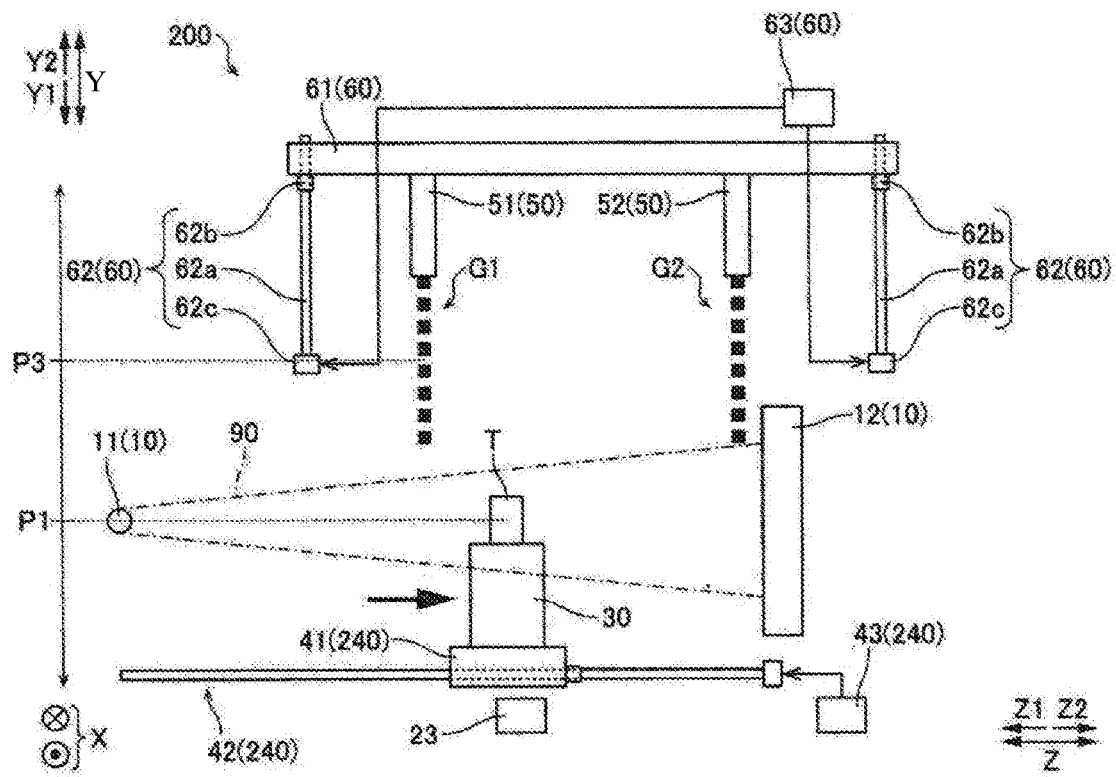
FIG. 11 is a diagram showing a state of moving the object stage across the first grating in the optical axis direction in a state in which the first grating is retracted to the noninterference position in the radiation phase contrast imaging apparatus according to the second embodiment.

Next, as shown in FIG. 11, the control unit 221 controls the moving mechanism 240 to move the object T and the object stage 30 across the first grating G1 in the optical axis direction in a state in which the first grating G1 is at the noninterference position P3. Specifically, the control unit 221 drives the drive unit 43 to move the object stage 30 holding the object T in the Z2-direction by the linear motion mechanism 42 by a predetermined distance (necessary for the object T to cross the first grating G1 in the optical axis direction).

Figure 12:
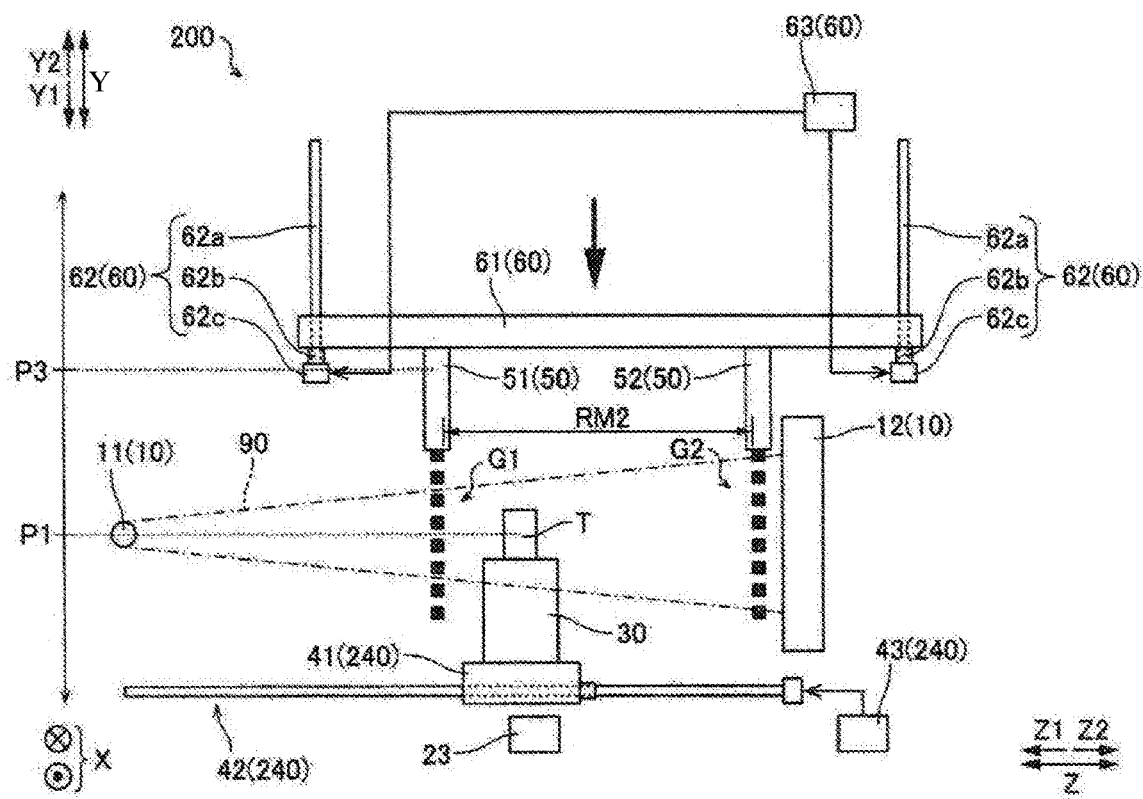
FIG. 12 is a diagram showing a state of returning the first grating to the imaging position in a state in which the object stage is moved in the optical axis direction across the first grating in the radiation phase contrast imaging apparatus according to the second embodiment.

Then, as shown in FIG. 12, the control unit 221 controls the retraction mechanism 60 to return the first grating G1 on the X-ray source 11 side (Z1 side) than the object stage 30 in the optical axis direction and at the noninterference position P3 to the imaging position P1. More specifically, the control unit 221 drives the drive unit 63 to move the first grating G1 held by the grating holder 51 in the Y1-direction by a predetermined distance (distance between P3 and P1) (necessary for returning the first grating G1 to the imaging position P1) by the linear motion mechanism 62.

As described above, in the second embodiment, in a state in which the first grating G1 is retracted to the noninterference position P3 by the retraction mechanism 60, the moving mechanism 40 is configured to move the object stage 30 across the first grating G1 in the optical axis direction.

Other configurations of the second embodiment are the same as those of the first embodiment.

Effects of Second Embodiment

In the second embodiment, the following effects can be obtained.

In the second embodiment, as described above, the X-ray phase imaging apparatus 200 is provided with the moving mechanism 240 that moves the object stage 30 holding the object T. The moving mechanism 240 can move the object stage 30 to the X-ray source 11 side (Z1 side) of the first grating G1 and the second grating G2 side (Z2 side) of the first grating G1. With this, in the same manner as in the X-ray phase imaging apparatus 100 of the first embodiment, it is possible to extend the variable range of the scaling ratio of the object T while securing the visibility in the phase contrast image.

Further, in the second embodiment, as described above, the X-ray phase imaging apparatus 200 is configured to retract the first grating G1 in a direction (Y2-direction) different from the optical axis direction up to the noninterference position P3 where the object T and the first grating G1 do not interfere in the optical axis direction when moving the object stage 30 across the first grating G1 in the optical axis direction (Z-direction) of the X-ray. With this configuration, in the same manner as in the X-ray phase imaging apparatus 100 of the first embodiment, it is possible to suppress the interference between the object T and the first grating G1 when moving the object stage 30 across the first grating G1 in the optical axis direction of the X-ray.

Further, in the second embodiment, as described above, the X-ray phase imaging apparatus 200 is equipped with a retraction mechanism 60 that retracts the first grating G1 in a direction (Y2-direction) different from the optical axis direction (Z-direction). In a state in which the first grating G1 is retracted to the noninterference position P3 by the retraction mechanism 60, the moving mechanism 240 is configured to move the object stage 30 across the first grating G1 in the optical axis direction. With this, it is possible that the retraction mechanism 60 and the moving mechanism 240 can be simplified in configuration specialized for the function to retract them to the noninterference position P3 and the function to move the first grating G1 in the optical axis direction, respectively. As a result, while suppressing the complication of the apparatus configuration, a device configuration for moving the object stage 30 across the first grating G1 in the optical axis direction of the X-ray (simplification of the moving mechanism) can be realized without causing interference between the object T and the first grating G1.

Further, in the second embodiment, as described above, the X-ray phase imaging apparatus 200 further includes the position detection unit 23 for detecting the position of the object T. The moving mechanism 240 is configured to move the object stage 30 to a position other than a return position of the first grating G1 retraced by the retraction mechanism 60 based on the position of the object T detected by the position detection unit 23. With this, when returning the first grating G1 retracted by the retraction mechanism 60 to the imaging position P1, it is possible to prevent the first grating G1 from coming into contact with the object T and the object stage 30.

Other effects of the second embodiment are the same as those of the first embodiment.

[Modifications]

It should be understood that the embodiments disclosed here are examples in all respects and are not restrictive. The scope of the present invention is shown by the scope of the claims rather than the descriptions of the embodiments described above, and include all changes (modifications) within the meaning of equivalent and the scope of claims.

For example, in the first embodiment, an example is shown in which the object stage 30 is configured to retract in the Y1-direction up to the noninterference position P2 where the object T and the first grating G1 do not interfere in the optical axis direction, but the present invention is not limited thereto. In the present invention, it may be configured such that the object stage is retracted in the Y2-direction or retracted in the X-direction.

For example, in the second embodiment, an example is shown in which the first grating G1 is configured to retract in the Y2-direction up to the noninterference position P3 where the object T and the first grating G1 do not interfere in the optical axis direction. The present invention, however, is not limited thereto. In the present invention, it may be configured such that the object stage is retracted in the Y1-direction or retracted in the X-direction.

In the first embodiment, the direction in which the object stage 30 is supported and the direction in which the object stage 30 is retracted are both the same direction (Y1-direction), but the present invention is not limited thereto. In the present invention, the direction in which the object stage is supported and the direction in which the object stage is retracted may be different from each other.

In the second embodiment, the direction in which the first grating G1 is supported and the direction in which the first grating G1 is retracted are both the same direction (Y2-direction), but the present invention is not limited thereto. In the present invention, the direction in which the first grating is supported and the direction in which the first grating is retracted may be different from each other.

Also, in the first embodiment, an example in which the object stage 30 is retracted by the moving mechanism 40 is shown, while in the second embodiment described above, an example in which the first grating G1 is retracted by the retraction mechanism 60 is shown. However, the present invention is not limited thereto. In the present invention, both the configuration of retracting the object stage by the moving mechanism of the first embodiment and the configuration of retracting the first grating by the retraction mechanism of the second embodiment may be provided.

Further, in the first and second embodiments, the example in which the linear motion mechanisms 42, 44, and 62 are each configured by a ball screw mechanism is shown, but the present invention is not limited to this. In the present invention, the linear motion mechanism may be configured by, for example, a belt pulley mechanism, a rack pinion mechanism, or the like, as long as it is a mechanism for linearly moving in a predetermined direction.

Further, in the aforementioned first and second embodiments, the example in which the object stage 30 can be moved to the first range R1 on the X-ray source 11 side (Z1 side) of the first grating G1 and the second range R2 side in which the distance GL from the first grating G1 is equal to the first range R1 on the second grating G2 side (Z2 side) of the first grating G1 is shown, but the present invention is not limited thereto. In the present invention, the range to move the object stage 30 may be configured to be different from each other between the X-ray source 11 side (Z1 side) of the first grating G1 and the second grating G2 side (Z2 side) of the first grating G1.

Figure 13:
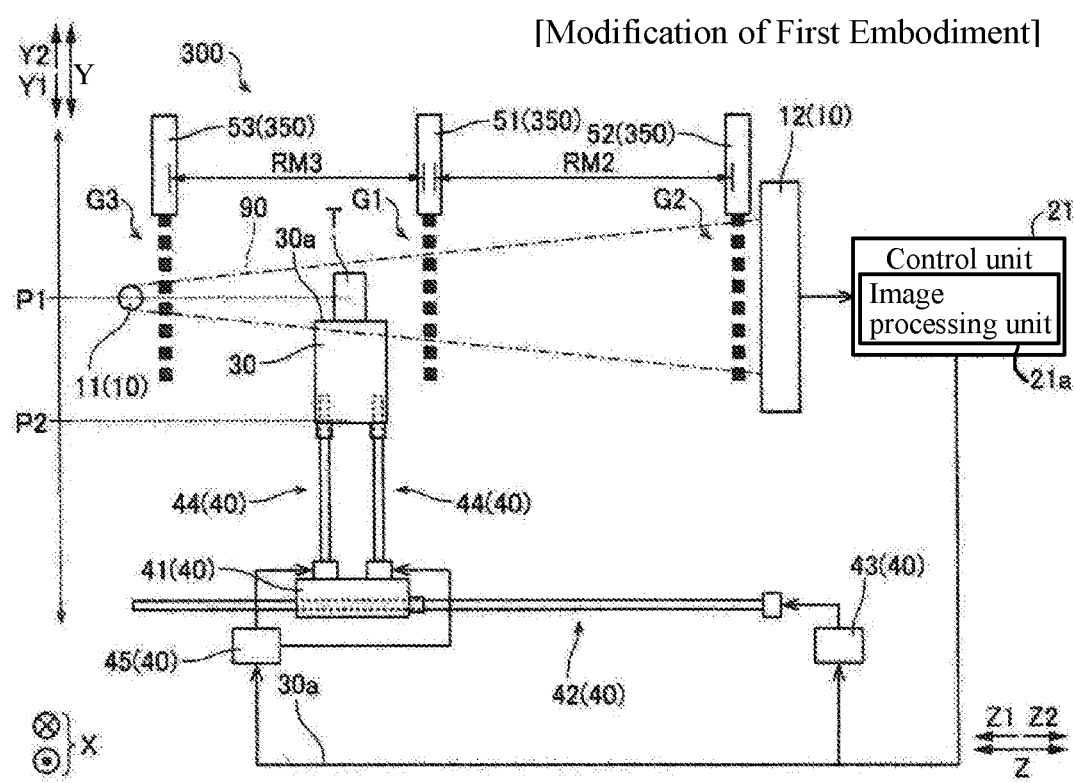
FIG. 13 is a schematic diagram showing an overall configuration of a radiation phase contrast imaging apparatus according to a modification of the first embodiment of the present invention.
Figure 14:
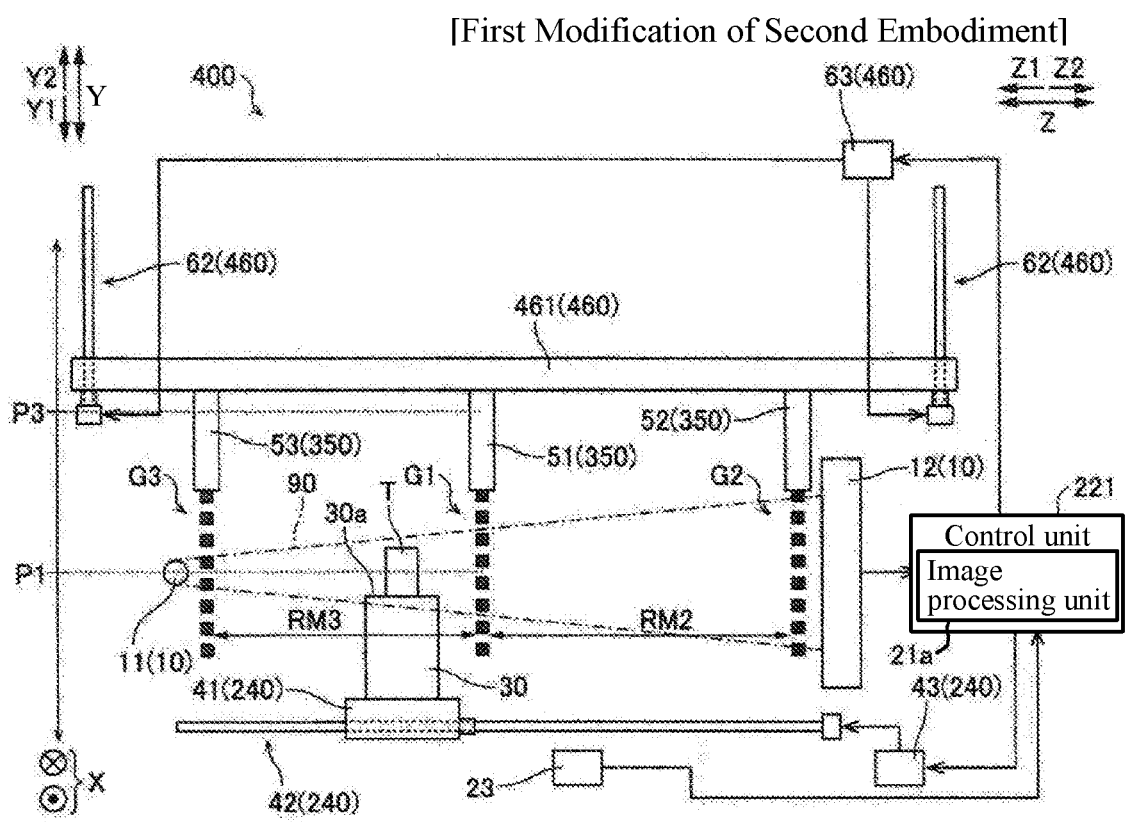
FIG. 14 is a schematic diagram showing an overall configuration of a radiation phase contrast imaging apparatus according to a first modification of the second embodiment of the present invention.

Further, in the aforementioned first and second embodiments, the example in which the plurality of gratings includes the first grating G1 and the second grating G2 is shown, but the present invention is not limited to this. In the present invention, in addition to the first grating and the second grating, between the X-ray source and the first grating, a third grating which is a grating (multi-slit) capable of micro-focusing the X-ray irradiated from the X-ray source may be further provided. For example, when the configuration of the first embodiment and the configuration of the second embodiment further include a third grating, it becomes a configuration of the X-ray phase imaging apparatus 300 according to the modification of the first embodiment shown in FIG. 13 and the X-ray phase imaging apparatus 400 according to the first modification of the second embodiment shown in FIG. 14. Note that the X-ray phase imaging apparatus 300 and the X-ray phase imaging apparatus 400 each are an example of the "radiation phase contrast imaging apparatus" recited in claims.

In addition to the configuration of the X-ray phase imaging apparatus 100, the X-ray phase imaging apparatus 300 further includes a third grating G3 and a grating holder 350. The grating holder 350 includes a grating holder 53 that holds the third grating G3 in addition to the grating holder 51 and the grating holder 52. The third grating G3 is arranged in the vicinity of the X-ray source 11. Therefore, in the X-ray phase imaging apparatus 300, between the X-ray source 11 and the first grating G1, the object stage 30 can be moved in the optical axis direction within the range RM3 between the first grating G1 and the third grating G3.

In addition to the configuration of the X-ray phase imaging apparatus 200, an X-ray phase imaging apparatus 400 further includes a third grating G3 and a grating holder 350 including the grating holder 53. Further, unlike the X-ray phase imaging apparatus 200, the X-ray phase imaging apparatus 400 is equipped with a retraction mechanism 460 including a hanging portion 461 that can suspend the third grating G3 in addition to the first grating G1 and the second grating G2.

In the X-ray phase imaging apparatus 400 according to the first modification of the second embodiment, similarly to the X-ray phase imaging apparatus 300 of the modification of the first embodiment, between the X-ray source 11 and the first grating G1, the object stage 30 is configured to be movable in the optical axis direction within the range RM3 between the first grating G1 and the third grating G3.

Figure 15:
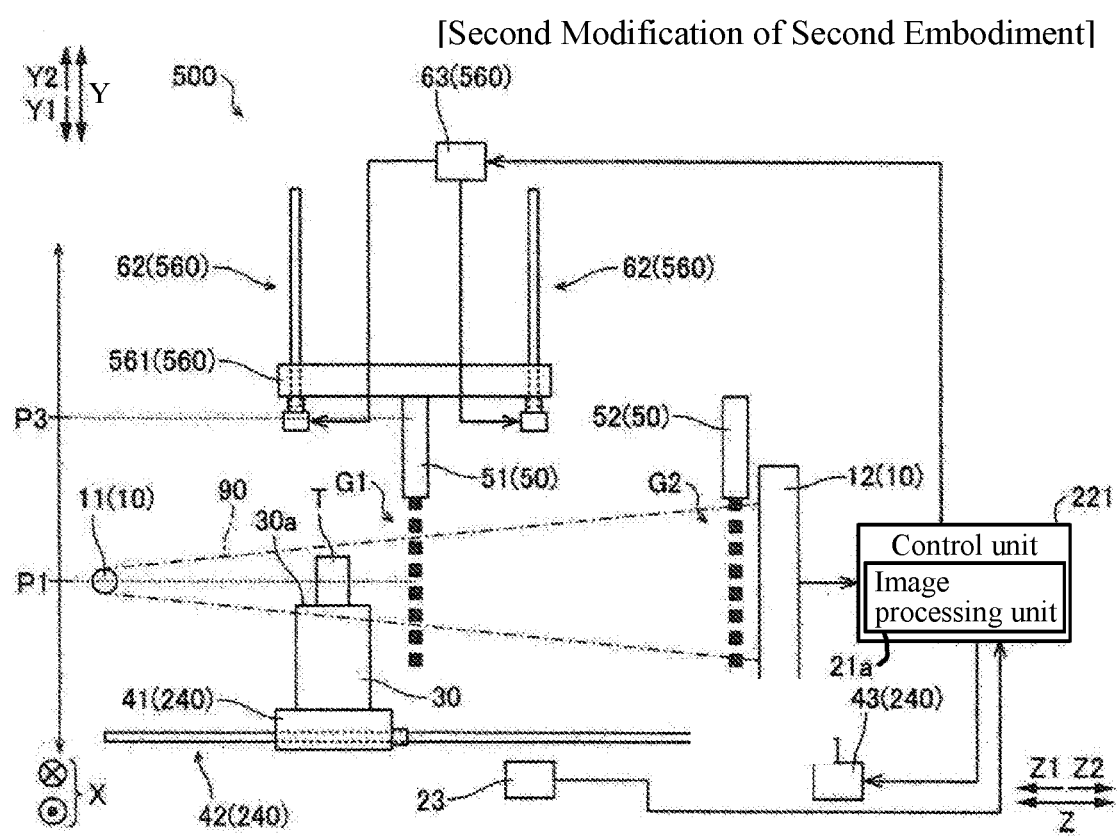
FIG. 15 is a schematic diagram showing an overall configuration of a radiation phase contrast imaging apparatus according to a second modification of the second embodiment of the present invention.

Further, in the second embodiment, an example in which the first grating G1 and the second grating G2 are moved in the Y2-direction by the retraction mechanism 60. However, the present invention is not limited to this. In the present invention, like the X-ray phase imaging apparatus 500 of the second modification of the second embodiment shown in FIG. 15, only the first grating G1 may be moved in the Y2-direction. Note that the X-ray phase imaging apparatus 500 is an example of the "radiation phase contrast imaging apparatus" recited in claims.

Unlike the X-ray phase imaging apparatus 200 equipped with the retraction mechanism 60 including a hanging portion 61 for hanging the grating holder 51 and the grating holder 52, an X-ray phase imaging apparatus 500 is provided with a retraction mechanism 560 including a hanging portion 561. The hanging portion 561 is configured to hang only the grating holder 51 out of the grating holder 51 holding the first grating G1 and the grating holder 52 for holding the second grating G2.

Further, in the second embodiment, an example in which the first grating G1 is configured to retract to the noninterference position P3 when moving the object stage 30 across the first grating G1 in the optical axis direction (Z-direction) of the X-ray, but the present invention is not limited thereto. In the present invention, it can also be used as an apparatus configuration configured to generate an absorption image based on the intensity of the X-ray in a state in which the grating is retracted by the retraction mechanism.

Further, in the first and second embodiments, an example in which the first grating G1 is a phase grating to form a self-image by the Talbot effect, but the present invention is not limited thereto. In the present invention, it is enough that the self-image is a stripe pattern, so an absorption grating may be used instead of the phase grating. When an absorption grating is used, a region (non-interferometer) in which a stripe pattern simply occurs due to optical conditions such as a distance and a region (interferometer) where a self-image is generated by a Talbot effect are generated.

Further, in the first and second embodiments, an example is shown in which the first grating G1 includes a slit G1$a$ and an X-ray absorption portion G1$b$ arranged in the Y-direction in a predetermined period (grating pitch) d1 and each slit G1a and X-ray absorption portion G1b are formed so as to extend in the X direction, but the present invention is not limited thereto. In the present invention, the first grating G1 may include a slit and an X-ray absorption portion arranged in the X-direction in a predetermined period (grating pitch) and each slit and X-ray absorption portion may be formed so as to extend in the Y-direction.

Further, in the first and second embodiments, an example is shown in which the second grating G2 includes a slit G2a and an X-ray absorption portion G2b arranged in the Y-direction in a predetermined period (grating pitch) d2 and each slit G2a and X-ray absorption portion G2b are formed so as to extend in the X-direction, but the present invention is not limited thereto.

In the present invention, the second grating G2 may include a slit and an X-ray absorption portion arranged in the X-direction in a predetermined period (grating pitch) and each slit and X-ray absorption portion may be formed so as to extend in the Y-direction.

The invention claimed is:

1. A radiation phase contrast imaging apparatus comprising:
    an image signal generation system including an X-ray source and an image signal detector for detecting an image signal based on X-rays irradiated from the X-ray source;
    a plurality of gratings including a first grating positioned so that the X-rays from the X-ray source may be irradiated thereon and a second grating arranged between the first grating and the image signal detector;
    an image processing unit configured to generate a phase contrast image due to a phase shift of the X-ray caused by an object arranged between the X-ray source and the image signal detector;
    an object stage configured to hold the object; and
    a moving mechanism configured to move the object stage to an X-ray source side of the first grating and a second grating side of the first grating in an optical axis direction of the X-ray across the first grating.

2. The radiation phase contrast imaging apparatus as recited in claim 1,
    wherein when moving the object stage across the first grating in the optical axis direction, at least one of the object stage and the first grating is retracted in a direction different from the optical axis direction up to a noninterference position at which the object and the first grating do not interfere in the optical axis direction.

3. The radiation phase contrast imaging apparatus as recited in claim 2,
    wherein a direction in which the object stage is supported and a direction in which the first grating is supported are different from each other.

4. The radiation phase contrast imaging apparatus as recited in claim 2,
    wherein the moving mechanism is configured to retract the object stage in a direction different from the optical axis direction and move the object stage across the first grating in the optical axis direction.

5. The radiation phase contrast imaging apparatus as recited in claim 2,
    further comprising a retraction mechanism configured to retract the first grating in a direction different from the optical axis direction,
    wherein the moving mechanism is configured to move the object stage across the first grating in the optical axis direction in a state in which the first grating is retracted to the noninterference position by the retraction mechanism.

6. The radiation phase contrast imaging apparatus as recited in claim 5,
    further comprising a position detection unit configured to detect a position of the object,
    wherein the moving mechanism is configured to move the object stage to a position other than a return position of the first grating retraced by the retraction mechanism based on the position of the object detected by the position detection unit.

7. The radiation phase contrast imaging apparatus as recited in claim 1,
    wherein the moving mechanism is configured to move the object stage to a first range on the X-ray source side of the first grating and a second range in which a distance from the first grating is substantially equal to that of the first range on the second grating side of the first grating.

8. The radiation phase contrast imaging apparatus as recited in claim 1,
    further comprising a third grating arranged between the X-ray source and the first grating for enhancing coherence of the X-ray irradiated from the X-ray source,
    wherein the moving mechanism is configured to move the object stage in the optical axis direction within a range from the first grating to the third grating and within a range from the first grating to the second grating.

* * * * *